(12) United States Patent
Hayashi et al.

(10) Patent No.: US 7,846,151 B2
(45) Date of Patent: Dec. 7, 2010

(54) MEDICAL LASER APPARATUS

(75) Inventors: Kenichi Hayashi, Gamagori (JP); Tsuyoshi Yamada, Toyota (JP)

(73) Assignee: Nidek Co., Ltd., Gamagori-shi (JP)

( * ) Notice: Subject to any disclaimer, the term of this patent is extended or adjusted under 35 U.S.C. 154(b) by 794 days.

(21) Appl. No.: 11/316,836

(22) Filed: Dec. 27, 2005

(65) Prior Publication Data

US 2006/0161140 A1    Jul. 20, 2006

(30) Foreign Application Priority Data

Jan. 5, 2005    (JP) ............................. 2005-000891

(51) Int. Cl.
*A61B 18/18* (2006.01)
(52) U.S. Cl. .................. 606/4; 606/5; 372/20; 359/328
(58) Field of Classification Search ....................... None
See application file for complete search history.

(56) References Cited

U.S. PATENT DOCUMENTS

| | | | | |
|---|---|---|---|---|
| 5,144,630 A | * | 9/1992 | Lin | 372/22 |
| 5,235,605 A | * | 8/1993 | Rines et al. | 372/20 |
| 5,321,718 A | * | 6/1994 | Waarts et al. | 372/108 |
| 5,410,560 A | * | 4/1995 | Taira | 372/21 |
| 5,414,548 A | * | 5/1995 | Tachikawa et al. | 398/87 |
| 6,200,309 B1 | * | 3/2001 | Rice et al. | 606/10 |
| 6,210,401 B1 | * | 4/2001 | Lai | 606/12 |
| 6,590,698 B1 | * | 7/2003 | Ohtsuki et al. | 359/326 |
| 6,613,042 B1 | * | 9/2003 | Tankovich et al. | 606/10 |
| 6,636,537 B2 | | 10/2003 | Takada | |
| 6,885,683 B1 | * | 4/2005 | Fermann et al. | 372/25 |
| 2002/0095142 A1 | * | 7/2002 | Ming | 606/5 |
| 2004/0170355 A1 | * | 9/2004 | Yamauchi et al. | 385/37 |
| 2004/0181212 A1 | * | 9/2004 | Kurimura et al. | 606/10 |
| 2004/0213301 A1 | * | 10/2004 | Sharma et al. | 372/3 |
| 2005/0058163 A1 | * | 3/2005 | Kane et al. | 372/10 |
| 2006/0129210 A1 | * | 6/2006 | Cantin et al. | 607/88 |

FOREIGN PATENT DOCUMENTS

| JP | A 2002-151774 | 5/2002 |
|---|---|---|
| JP | A 2004-126131 | 4/2004 |
| JP | A 2004-321507 | 11/2004 |

* cited by examiner

*Primary Examiner*—Henry M Johnson, III
*Assistant Examiner*—Lynsey Crandall
(74) *Attorney, Agent, or Firm*—Oliff & Berridge, PLC

(57) ABSTRACT

A medical laser apparatus for irradiating an affected tissue with a laser beam to treat the affected tissue, comprises: a laser source unit which emits an infrared beam as a fundamental wave having a spectral bandwidth; a wavelength demultiplexing optical system which spatially demultiplexes the emitted infrared beam by wavelengths; a wavelength converting optical system including a wavelength converting element disposed in correspondence with an optical path position of each of the demultiplexed infrared beams and for converting each of the infrared beams to a visible beam as a second harmonic wave; a wavelength multiplexing optical system which multiplexes the visible beams obtained by the conversion; and a delivery optical system which guides the multiplexed visible beams to the affected tissue.

7 Claims, 6 Drawing Sheets

MEDICAL LASER APPARATUS

BACKGROUND OF THE INVENTION

1. Field of the Invention

The present invention relates to a medical laser apparatus for irradiating an affected tissue with a laser beam to treat the affected tissue.

2. Description of Related Art

As a laser apparatus capable of outputting a visible laser beam for treatment by continuous wave oscillation, for example, there is a known laser apparatus that converts an infrared laser beam as a fundamental wave emitted from an Nd:YAG laser source or the like to a visible laser beam as a second harmonic wave by a wavelength converting element and outputs the visible laser beam. In recent years, a laser apparatus is proposed, which shifts the infrared laser beam emitted from the Nd:YAG laser source or the like to a long wavelength side by a Raman fiber, converts the Raman-shifted infrared laser beam to a visible laser beam of orange color or red color which is preferable for photocoagulation treatment by a wavelength converting element, and outputs the visible laser beam.

It is desirable to output a visible laser beam for treatment used for ophthalmologic photocoagulation treatment or the like with high energy of 1 W or higher. However, a nonlinear crystal as a wavelength converting element for converting an infrared laser beam to a visible laser beam has a low damage threshold and cannot receive an infrared laser beam of high energy, so that it is difficult to output a visible laser beam of high energy. In addition, the spectral bandwidth (half width) of the Raman-shifted infrared laser beam tends to widen, so that the wavelength conversion efficiency of the wavelength converting element tends to deteriorate. Since the center wavelength of the Raman-shifted infrared laser beam easily fluctuates according to temperature and the like, the wavelength conversion efficiency of the wavelength converting element constructed so as to be adapted to a predetermined center wavelength also tends to deteriorate.

SUMMARY OF THE INVENTION

In view of the problems of the conventional techniques, a technical object of the present invention is to provide a medical laser apparatus capable of outputting a visible laser beam of high energy even in the case of performing wavelength conversion on an infrared laser beam by a wavelength converting element having a low damage threshold. Another technical object is to provide a medical laser apparatus capable of outputting a visible laser beam of high energy even in the case of performing wavelength conversion on an infrared laser beam having a wide spectral bandwidth and an infrared laser beam whose center wavelength fluctuates.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To solve the above issues, the present invention is characterized in the following structures. A medical laser apparatus for irradiating an affected tissue with a laser beam to treat the affected tissue, comprises: a laser source unit which emits an infrared beam as a fundamental wave having a spectral bandwidth; a wavelength demultiplexing optical system which spatially demultiplexes the emitted infrared beam by wavelengths; a wavelength converting optical system including a wavelength converting element disposed in correspondence with an optical path position of each of the demultiplexed infrared beams and for converting each of the infrared beams to a visible beam as a second harmonic wave; a wavelength multiplexing optical system which multiplexes the visible beams obtained by the conversion; and a delivery optical system which guides the multiplexed visible beams to the affected tissue.

DETAILED DESCRIPTION OF THE PREFERRED EMBODIMENTS

Figure 1:
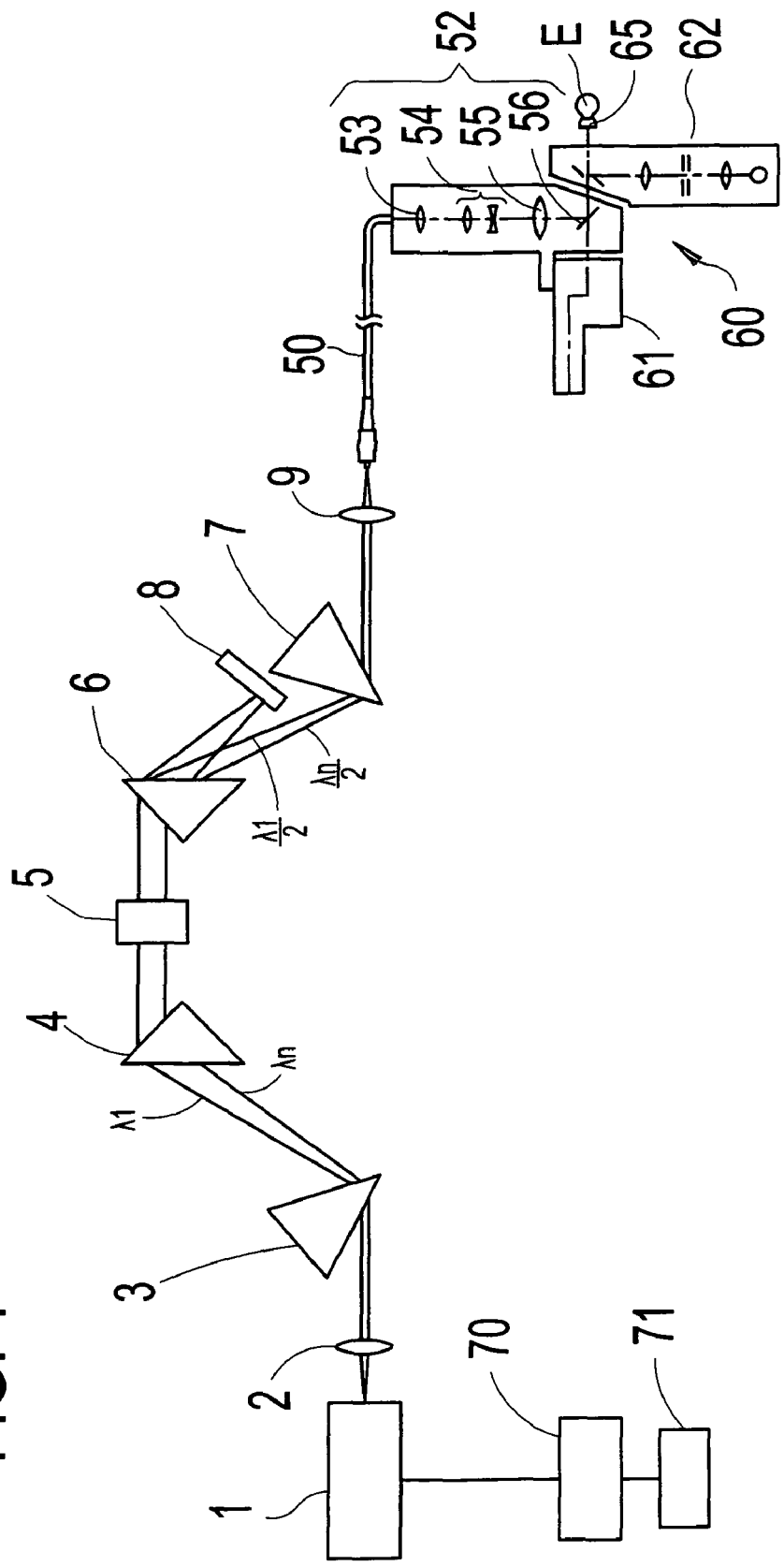
FIG. 1 is a schematic configuration view of a laser apparatus in a first embodiment of the present invention.

Embodiments of the present invention will be described hereinbelow with reference to the drawings. FIG. 1 is a schematic configuration view of a laser apparatus in a first embodiment of the invention. In FIG. 1, a laser source unit (laser oscillator) 1 that emits an infrared laser beam is connected to a control unit 70. The control unit 70 is connected to a control panel 71 for setting treatment parameters such as output energy of a laser beam, coagulation time, and the like.

Figure 2:
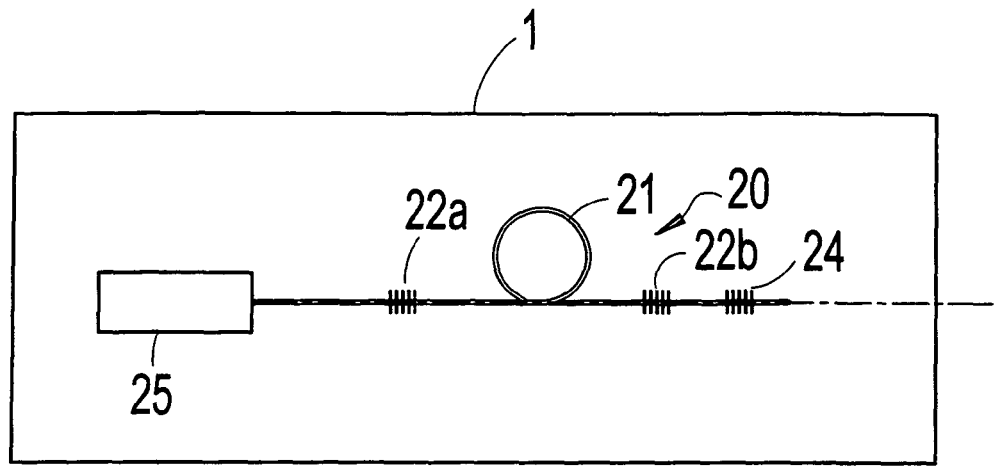
FIG. 2 is a schematic configuration view of an internal structure of a laser source unit.

FIG. 2 is a schematic configuration view showing the internal structure of the laser source unit 1. A laser source (pumping source) 25 disposed in the laser source unit 1 is, for example, a Yb-doped fiber laser source and emits an infrared beam having the center wavelength of 1064 nm. A Raman fiber 20 is an optical fiber (nonlinear optical fiber) 21 using silica ($SiO_2$) as a base and whose core part is doped with titanium oxide ($TiO_2$). For the optical fiber 21, a pair of fiber Bragg gratings (hereinbelow, FBG) 22a and 22b that reflect a primary stokes beam having the center wavelength of 1180 nm generated by stimulated Raman scattering are formed. On the output terminal side of the optical fiber 21, an FBG 24 which reflects the infrared beam having the center wavelength of 1064 nm and transmits the infrared beam having the center wavelength of 1180 nm is formed. The optical fiber 21 in the present embodiment is a polarization maintaining fiber that maintains linear polarization of a passing beam. In place of using the optical fiber 21 as the polarization maintaining fiber, a polarization element which polarizes a beam to a linear polarization beam may be provided on the inside or outside of the laser source unit 1.

Figure 3:
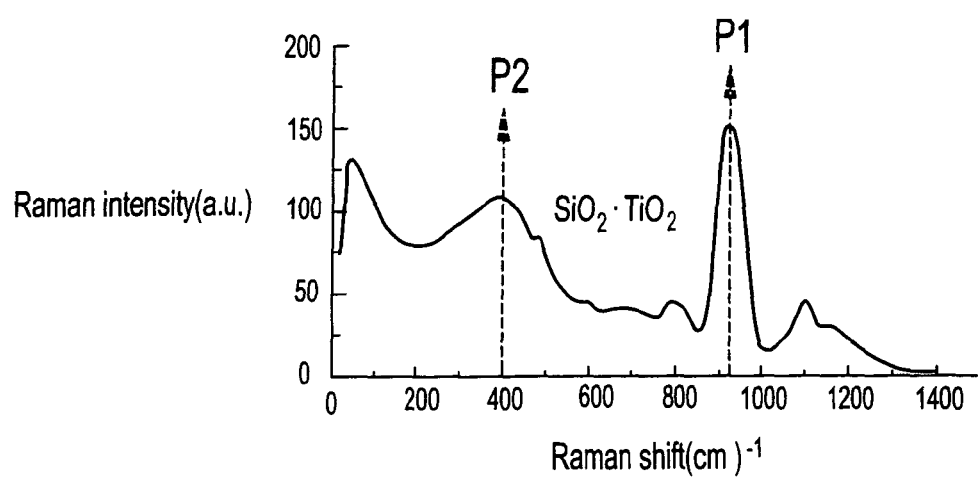
FIG. 3 is a view showing stimulated Raman scattering characteristics of a Raman fiber.

FIG. 3 shows stimulated Raman scattering characteristics of the $TiO_2$-doped, $SiO_2$-based optical fiber. As shown in FIG. 3, in the $TiO_2$-doped, $SiO_2$-based optical fiber, peaks of stimulated Raman scattering appear at about 925 $cm^{-1}$ and about 400 $cm^{-1}$. Therefore, the stimulated Raman scattering having a peak at the wavelength of 1180 nm corresponding to a Raman shift P1 of 925 $cm^{-1}$ is obtained by the infrared excitation beam having the center wavelength of 1064 nm. By providing a resonator by the FBG 22a of total reflection (reflectance of 99% or higher) and the FBG 22b for output of partial transmission (reflectance of about 85%) with respect to the infrared beam having the center wavelength of 1180 nm, the infrared beam having the center wavelength of 1180 nm is extracted. The infrared beam having the center wavelength of 1064 nm propagates through the optical fiber 21 and is turned back by the FBG 24 so that the stimulated Raman scattering in the optical fiber 21 is made more active.

By performing the wavelength conversion on the infrared beam having the center wavelength of 1180 nm as the fundamental wave from the laser source unit 1 to the second harmonic wave, a visible orange laser beam having the center wavelength of 590 nm suitable for medical treatment use (particularly, suitable for ophthalmologic photocoagulation treatment) is generated. Alternately, the Raman fiber 20 may be constructed so as to generate an infrared beam having the center wavelength of 1240 nm by adding a pair of FBGs to obtain stimulated Raman scattering having a peak at the wavelength of 1240 nm corresponding to a Raman shift P2 of about 400 cm$^{-1}$ by the primary stokes beam having the center wavelength of 1180 nm by using the peak of stimulated Raman scattering around 400 cm$^{-1}$ in FIG. 3. In this case, by performing the wavelength conversion on the infrared beam having the center wavelength of 1240 nm as the fundamental wave from the laser source unit 1 to the second harmonic wave, a visible red laser beam having the center wavelength of 620 nm is generated.

In an optical path extending from the laser source unit 1 to a patient' eye E, a lens 2, a demultiplexing (dispersion) prism 3 and a deflection prism 4 as a wavelength demultiplexing (dispersion) optical system, a wavelength converting element 5 as a wavelength converting optical system, a deflection prism 6 and a multiplexing (combining) prism 7 as a wavelength multiplexing (combining) optical system, a condenser lens 9, an optical fiber 50, and a delivery optical system 52 are disposed. In a position where the infrared beam is absorbed before the multiplexing prism 7, a beam stopper 8 is disposed.

The infrared beam (for example, the infrared beam having the center wavelength of 1180 nm) from the laser source unit 1 is converted to a parallel beam by the lens 2, and the parallel beam is spatially demultiplexed (dispersed) at wavelengths by the demultiplexing prism 3. The infrared beam is Raman-shifted and its spectral bandwidth is widened (for example, the spectral bandwidth is ±1.0 nm). Although the infrared beam has actually a continuous wavelength distribution, it is assumed for easier explanation that beams of discrete wavelengths of $\lambda 1, \lambda 2, \ldots, \lambda i, \ldots,$ and $\lambda n$ ($\lambda 1$ is on the shortest wavelength side, $\lambda i$ is the center wavelength, and $\lambda n$ is the longest wavelength side) enter the demultiplexing prism 3 (for example, when the demultiplexing interval is the wavelength of 0.1 nm, the entered beam is demultiplexed to beams having wavelengths of $\lambda 1$ to $\lambda 21$). The beams having the wavelengths of $\lambda 1$ to $\lambda n$ are bent in different directions in accordance with the wavelength dispersiveness of the demultiplexing prism 3. The deflection prism 4 makes the infrared beams demultiplexed spatially by wavelengths almost parallel with each other. The deflection prism 4 may be omitted. The beams having the wavelengths $\lambda 1$ to $\lambda n$ which are made almost parallel to each other by the deflection prism 4 enter the wavelength converting element 5.

Figure 4A:
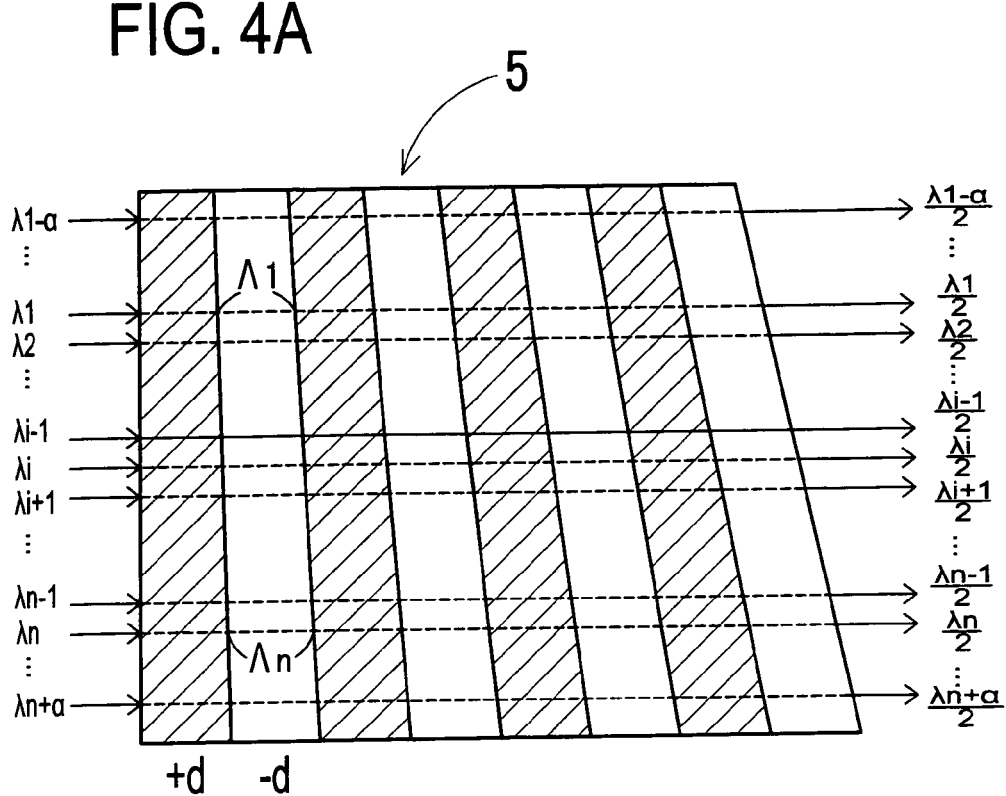
FIGS. 4A and 4B are views showing a structure of a wavelength converting element (quasi phase matching crystal)
Figure 4B:
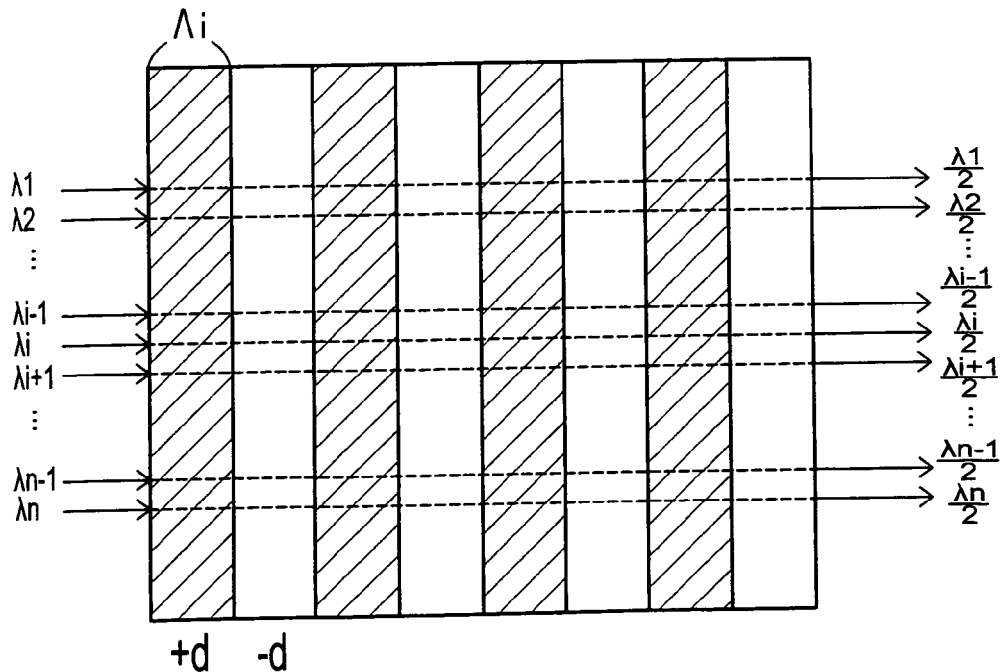

As the wavelength converting element 5, preferably, a nonlinear crystal (quasi phase matching crystal) such as MgO: PPLN crystal is used. The quasi phase matching crystal is an element for converting the fundamental wave to the second harmonic wave by employing a structure satisfying the phase matching condition by alternately inverting the polarization direction of a nonlinear optical material in periods of the coherence length. In FIGS. 4A and 4B, "+d" and "−d" show polarization.

Figure 5:
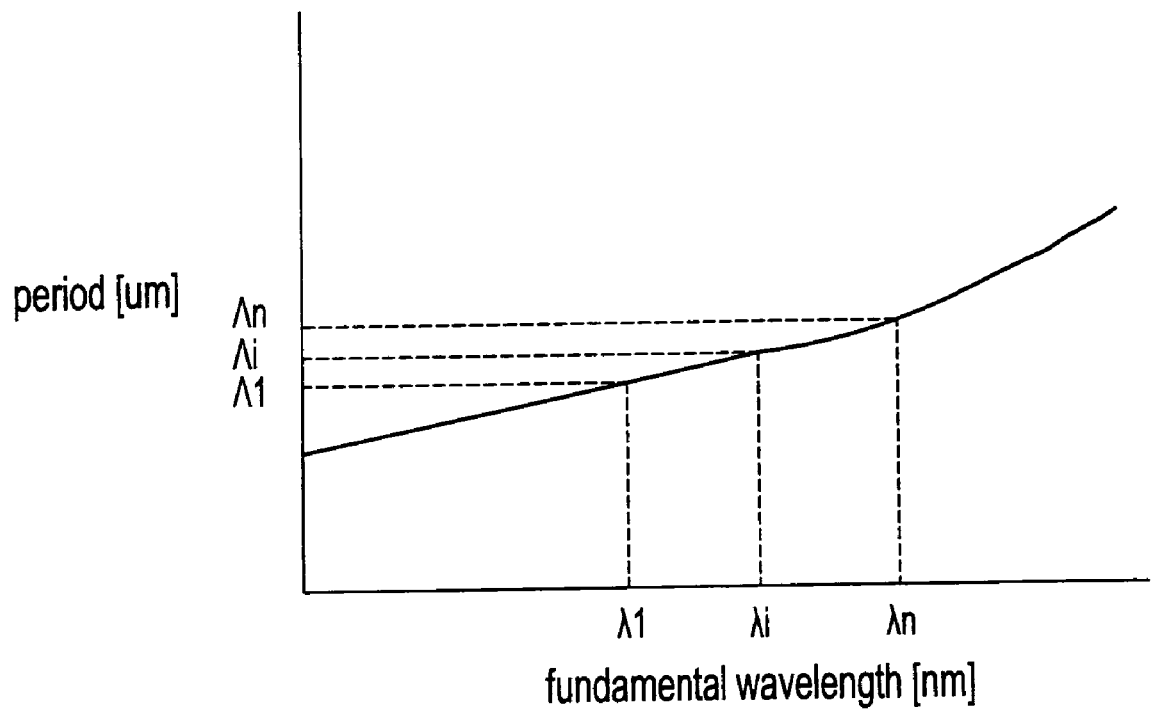
FIG. 5 is a graph showing a relation between a fundamental wave wavelength and a polarization inverting period.

FIG. 4A is a schematic view showing the structure of a wavelength converting element (quasi phase matching crystal) of the present embodiment. FIG. 5 shows the relation between the fundamental wave wavelength and the polarization inverting period of the quasi phase matching crystal. As shown in FIG. 5, the wavelength of each entered fundamental wave has proper polarization inverting periods Λ. On the basis of the relation, quasi phase matching crystals having structures of polarization inverting periods Λ1 to Λn corresponding to optical path positions of the beams having the wavelengths $\lambda 1$ to $\lambda n$ are integrally formed, thereby obtaining the wavelength converting element 5. Although the period structure is continuously changed so as to interpolate periods between the wavelengths $\lambda 1, \lambda 2, \ldots,$ and $\lambda n$ in the example, the period structure may be changed step by step in accordance with the wavelengths $\lambda 1, \lambda 2, \ldots,$ and $\lambda n$. Since each of wavelength converting parts in the polarization inverting periods Λ1 to Λn has an allowable width for the wavelength, the wavelength conversion can be performed without deteriorating efficiency so much. The polarization inverting period structure can be formed by the known electric field applying method or the like. Further, with respect to the shorter wavelength side and the longer wavelength side than the wavelengths $\lambda 1$ to $\lambda n$ as the spectral bandwidths of the fundamental wave, it is preferable to form polarization inverting period structures corresponding to the wavelengths in a wavelength range including fluctuations α(−α, +α) of the center wavelength $\lambda i$ of the fundamental wave. Preferably, each of the demultiplexing prism 3 and the deflection prism 4 as the wavelength demultiplexing optical system can demultiplex the beam to a spectral bandwidth including the fluctuation amount α of the center wavelength $\lambda i$.

Although it is preferable that the wavelength converting element as the wavelength converting optical system be integrally formed as shown in FIG. 4A, wavelength converting elements having polarization inverting period structures corresponding to optical path positions of the beams having the wavelengths $\lambda 1$ to $\lambda n$, which are separately formed, may be combined. The polarization inverting period is a period including an execution part in which polarities +d and −d are adjacent to each other. Consequently, the period structure is not limited to a period structure in which execution parts are always adjacent to each other as shown in FIGS. 4A and 4B. Although the output end of the wavelength converting element has an angle as shown in FIG. 4A with respect to the optical axis of the entered beam in the present embodiment, a structure in which the output end is orthogonal to the optical axis of the entered beam may be also employed.

As described above, by spatially demultiplexing the infrared beam by wavelengths and performing wavelength conversion by the wavelength converting element 5 having the structure as described above, the infrared beam of high energy can be entered even on the wavelength converting element having a low damage threshold. As a result, the visible beam of high energy can be output. Specifically, the infrared beam is demultiplexed to beams having the wavelengths $\lambda 1$ to $\lambda n$ by the demultiplexing prism 3, so that the energy density is also dispersed and the beam with dispersed energy density enters the wavelength converting element 5. Therefore, even when the infrared beam of high energy is emitted from the laser source unit 1, a damage is lessened in the wavelength converting parts corresponding to the wavelengths $\lambda 1$ to $\lambda n$ of the wavelength converting element 5, and high-efficient wavelength conversion can be performed. Consequently, the visible beam of high energy of 1 W or higher necessary for photocoagulation treatment or the like can be output. Though the spectral bandwidth of the infrared beam is wide, the wavelength converting element 5 can convert the infrared beam by wavelengths since it has the proper polarization inverting period structure in correspondence with the demultiplexed beams having the wavelengths $\lambda 1$ to $\lambda n$. Thus, the wavelength conversion efficiency improves as a whole.

Although the quasi phase matching crystal shown in FIG. 4A is used as the wavelength converting element in the present embodiment, alternatively, a quasi phase matching crystal having an uniform polarization inverting period structure as shown in FIG. 4B may be also employed. In such a quasi phase matching crystal, the polarization inverting period is set as $\Lambda i$ in correspondence with the center wavelength $\lambda i$. In the case where the beams having the wavelengths $\lambda 1$ to $\lambda n$ are entered on the quasi phase matching crystal, the wavelength conversion efficiency is the highest at the center wavelength $\lambda i$ and decreases toward the peripheral wavelengths $\lambda 1$ and $\lambda n$. However, displacement from the center wavelength $\lambda i$ to the peripheral wavelengths $\lambda 1$ and $\lambda n$ is not so large. Consequently, also in the case where the polarization inverting period is $\Lambda i$, the peripheral wavelengths $\lambda 1$ and $\lambda n$ are sufficiently converted. Further, the spectral bandwidth (half width) at each wavelength becomes narrower, and the conversion efficiency at each wavelength increases. Therefore, as compared with the case of performing wavelength conversion without spatially demultiplexing the entered beam, wavelength conversion can be performed more efficiently. In addition, since the beams spatially demultiplexed are entered also on the quasi phase matching crystal in FIG. 4B, the energy density of the beam at each wavelength is dispersed, and the infrared beam of high energy can be entered even on a quasi phase matching crystal having a low damage threshold. Since the spectral bandwidth at each wavelength is narrowed, wavelength conversion can be performed efficiently. For efficient wavelength conversion, the quasi phase matching crystal of FIG. 4A is more preferable.

Moreover, although the center wavelength $\lambda i$ of the infrared beam which is Raman shifted fluctuates according to the temperature and the like, only the passage position in the wavelength converting element 5 changes, so that the wavelength conversion is performed efficiently in the polarization inverting period structure part at each position. Consequently, it becomes unnecessary to take a countermeasure for precise temperature adjustment and additional wavelength fixation, and the apparatus configuration can be prevented from becoming complicated. In the case where the center wavelength $\lambda i$ largely fluctuates, by forming a polarization inverting period structure part having an allowance for the fluctuation amount $\alpha$ (from the part corresponding to the wavelength $\lambda 1-\alpha$ to the part corresponding to the wavelength $\lambda n+\alpha$) in the wavelength converting element 5, the efficient wavelength conversion can be maintained. For example, when the center wavelength $\lambda i$ is set to 1180 nm, the spectral bandwidth is set to $\pm 1.0$ nm, and the fluctuation $\alpha$ is set to $\pm 2.0$ nm, the polarization inverting period structure part is formed in accordance with the optical path position at each wavelength so as to lie in the wavelength range of 1177 nm to 1183 nm.

The second harmonic waves obtained by the wavelength conversion in the wavelength converting element 5 is multiplexed (combined) by the deflection prism 4 and the multiplexing prism 7. By making the deflection prism 4 and the multiplexing prism 7 multiplex the beams including a fluctuation amount in the case where the center wavelength fluctuates, it becomes unnecessary to correct the optical path after the wavelength conversion. Since the beam having the short wavelength passed through the deflection prism 6 is refracted more strongly than the beam having the long wavelength, the infrared beam as the fundamental wave which was not converted by the wavelength converting element 5 is split from the visible beam as the second harmonic wave and is absorbed by the beam stopper 8 provided in front of the multiplexing prism 7. Therefore, only the visible beams are multiplexed in the multiplexing prism 7. The multiplexed visible beam passes through the condenser lens 9 and enters the optical fiber 50.

The output end of the optical fiber 50 is connected to the delivery optical system 52 for guiding the visible beam to the patient's eye E. The delivery optical system 52 has a relay lens 53, a zoom lens 54 for changing the spot size of the visible beam, an objective lens 55, and a mirror 56 reflecting the visible beam toward the patient's eye E. The delivery optical system 52 is attached to a binocular microscope 61 of a slit lamp 60. The patient's eye E is illuminated by an illuminator 62 of the slit lamp 60. In photocoagulation treatment, the eyeground of the patient's eye E is irradiated with the visible beam guided by the delivery optical system 52 via a contact lens 65.

Although the prisms are used as the wavelength demultiplexing optical system and the wavelength multiplexing optical system in the first embodiment, the systems are not limited to the prisms but a transmission or reflection grating or a holography device can be also used.

Figure 6:
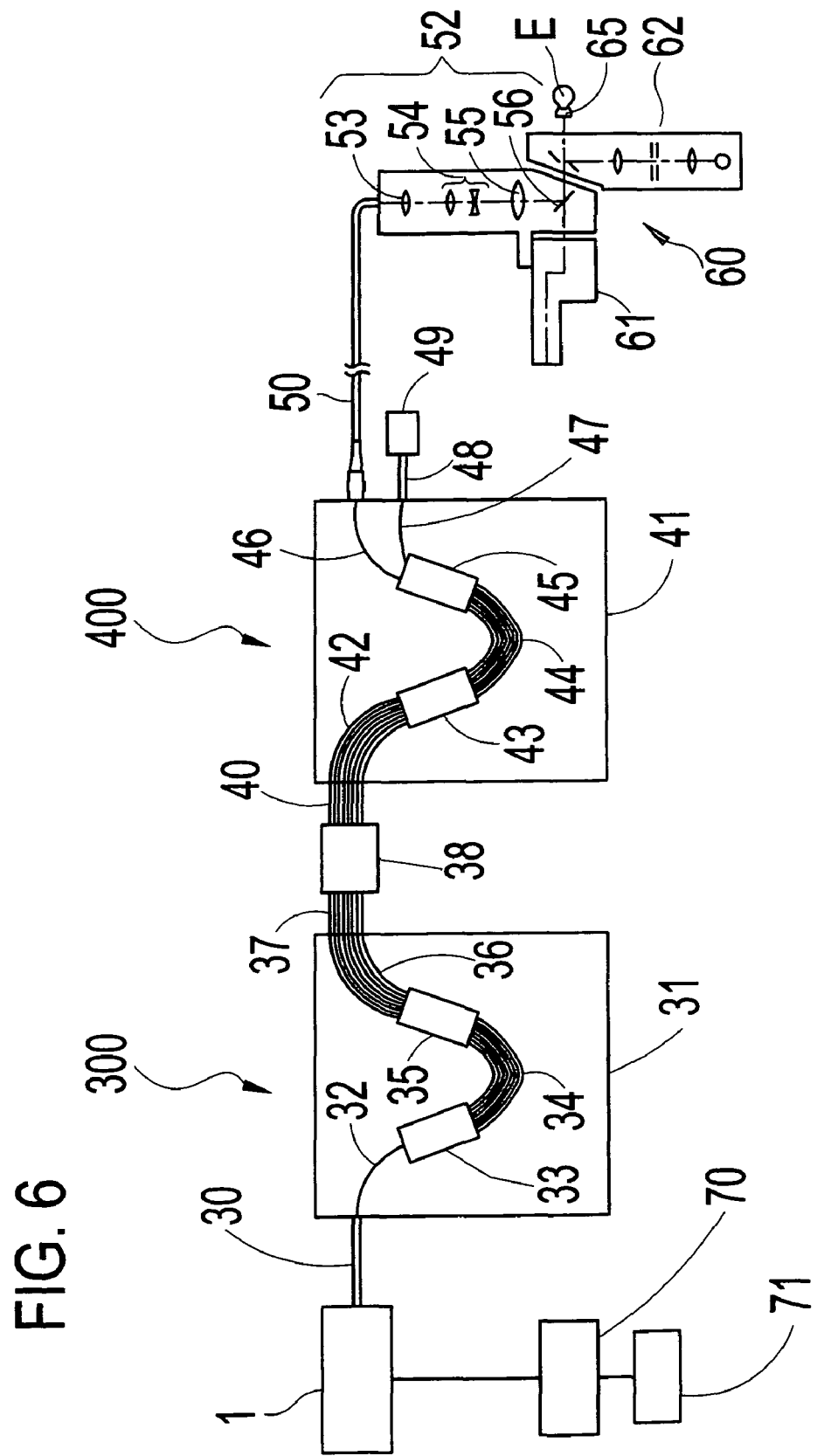
FIG. 6 is a schematic configuration view of a laser apparatus in a second embodiment of the present invention.

FIG. 6 is a schematic configuration view of a laser apparatus in a second embodiment of the invention. Since the components having the same reference numerals as those of FIG. 1 are basically the same, their description will not be repeated. In FIG. 6, 300 denotes an arrayed waveguide grating (AWG) as the wavelength demultiplexing optical system, and 400 denotes an AWG as the wavelength multiplexing optical system. The AWG is a wavelength (optical) multiplexer/demultiplexer that demultiplexes (disperses) one entered beam into beams by wavelengths and multiplexes (combines) a plurality of entered beams having different wavelengths into a single beam. The AWG is an optical circuit used in a wavelength division multiplex (WDM) system in the communication field (refer to, for example, US 2004/0170355 A1 (Japanese unexamined patent application publication No. 2004-126131) and the like), in which a waveguide is formed on a silicon substrate or a quartz substrate by a planer lightwave circuit (PLC) technique.

The configuration of the AWGs 300 and 300 will be briefly described. On a board 31 of the AWG 300, an input waveguide 32, a slab waveguide 33, arrayed waveguides 34 having different lengths, a slab waveguide 35, and output waveguides 36 from which beams are output are entered. On a board 41 of the AWG 400, an input waveguides 42 to which beams are entered, a slab waveguide 43, arrayed waveguides 44 having different lengths, a slab waveguide 45, a visible beam output waveguide 46, and an infrared beam output waveguide 47 are provided.

The infrared beam from the laser source unit 1 guided via an optical fiber 30 enters the input waveguide 32 and the slab waveguide 33. Since the slab waveguide 33 has the role of a diffraction grating, the entered infrared beam is scattered and dispersed by wavelengths. The dispersed infrared beams are distributed with the same phase to the array waveguides 34. When the infrared beams travel in the arrayed waveguides 34, a phase difference according to the wavelength length difference is given to the infrared beams by wavelengths. The infrared beams interfere each other in the slab waveguide 35 and are spectral-dispersed by wavelengths (in a manner similar to the above example, dispersed to the wavelength range of the wavelengths λ1 to λn, preferably, including the fluctuation amounts ±α of the center wavelength λi) and the resultant beams enter the output waveguides 36. At that time, the focal position shifts according to the wavelengths due to the phase difference given in the arrayed waveguides 34, so that the beams enter the waveguides provided in different positions according to the wavelengths. Therefore, the beams are distributed at the output waveguides 36 by wavelengths.

The output waveguides 36 in the AWG 300 and a wavelength converting element 38 are connected to each other via a plurality of optical fibers 37, and the wavelength converting element 38 and the input waveguides 42 in the AWG 400 are similarly connected to each other via a plurality of optical fibers 40. The wavelength converting element 38 has a configuration basically similar to that of the wavelength converting element 5 of the first embodiment and is obtained by integrally forming quasi phase matching crystals having the period structures of the polarization inverting periods corresponding to the optical positions of the wavelengths of beams guided by the plurality of optical fibers 37. The wavelength converting element 38 is characterized by having waveguide systems according to the wavelengths.

Figure 7A:
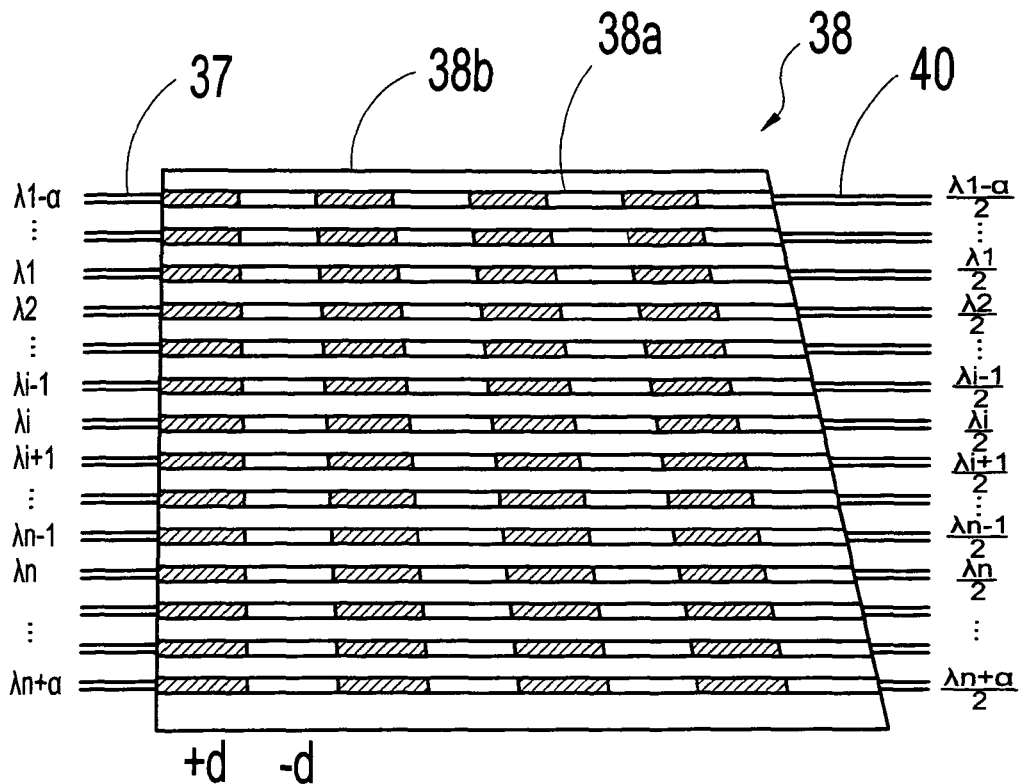
FIGS. 7A and 7B are schematic views of a wavelength converting element (quasi phase matching crystal) of a waveguide type.
Figure 7B:
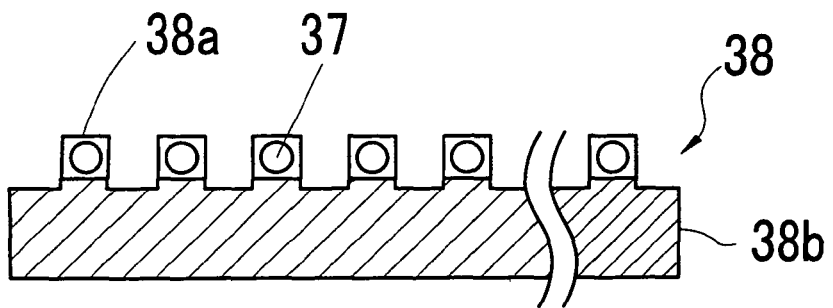

As shown in FIG. 7, slits are physically formed in the quasi phase matching crystals of the wavelength converting element 38 to form a plurality of projected parts 38a as waveguides by which wavelength conversion is realized. FIG. 7A is a view of the wavelength converting element 38 seen from a side of the optical path of the infrared beam, and FIG. 7B is a sectional view of the wavelength converting element 38 seen from the infrared beam input side. The projected parts 38a are formed in the optical path positions corresponding to the wavelengths. At the time of forming the quasi phase matching crystals used for the wavelength converting element 38, an LN ($LiNbO_3$) substrate (the substrate of the projected parts 38a) on which the period polarization inversion structure is formed in advance and an LT ($LiTaO_3$) substrate 38b having index of refraction lower than that of the LN substrate are joined to each other. After the substrates are directly joined to each other, the upper substrate serving as the waveguide is thinned by polishing, and the plurality of projected parts 38a are formed by using a dicing saw. By mirror-finishing the cut surfaces of the projected parts 38a, total reflection is brought about by the top surface and the right and left surfaces due to the different refraction indexes of the projected parts 38a and the air which comes into contact with the projected parts 38a. Since the LT substrate exists under the projected parts 38a, total reflection occurs also on the under surface of the projected parts 38a. Therefore, total reflection occurs on all of the top and under surfaces and the right and left surfaces of the projected part 38a, and the projected parts 38 serve as waveguides. The fiber 37 corresponding to each of the wavelengths of the entered infrared beams is fused to the input side of each of the projected parts 38a. The optical fiber 40 corresponding to each of the wavelengths of the visible beams to be output is fused to the output side of the projected part 38a. With such a configuration, each of the wavelengths is converted on the waveguide. The width of the projected part 38a is, preferably, 4 to 5 μm to form the waveguide.

Although the quasi phase matching crystal obtained by joining the LT substrate in which the period polarization inversion structure is formed to the LT substrate having a refractive index lower than that of the LT substrate is used in the embodiment, the present invention is not limited to the configuration. For example, an MgO-doped LN substrate may be used. Although the projected parts serving as the waveguides are formed by physical processing in the foregoing embodiment, the invention is not limited to the processing. Waveguides may be formed in the quasi phase matching crystals by, for example, the proton exchange method. In the method, waveguides are not formed by physical cutting like the projected parts 38a shown in FIG. 7B but are formed by performing chemical process on a quasi phase matching crystal to form waveguides in positions corresponding to the projected parts 38a. Therefore, according to the method, a plurality of waveguides are formed in the quasi phase matching crystal.

Although the waveguides are formed by forming slits in the wavelength converting element 38 in the second embodiment, the invention is not limited to the method. It is also possible to fuse a microlens array to each of the input end side and the output end side of the wavelength converting element 38, and fuse corresponding fibers to the microlens arrays to thereby match the optical axis of the entered beam and the optical axis of the beam to be output.

A plurality of visible beams obtained by the wavelength conversion in the wavelength converting element 38 enter the input waveguides 42 and are diffracted by the slab waveguide 43, and a phase difference is given at each wavelength in the arrayed waveguides 44. After that, the visible beams are multiplexed by the slab waveguide 45 and sent to the output waveguide 46, and the infrared beams are multiplexed and sent to the output waveguide 47.

In the AWG 400, the infrared beam as the fundamental wave whose wavelength is not converted by the wavelength converting element 38 is not guided to the delivery optical system 52 but is guided by the slave waveguide 45 to the output waveguide 47, and the infrared beam passes through the optical fiber 48 and is absorbed by the beam stopper 49. Another configuration may be employed in which only the infrared beam is extracted from a waveguide by a dichroic mirror disposed in the waveguide through which the visible beam and the infrared beam pass, and the infrared beam is absorbed. Similarly, only the visible beam may be guided to another waveguide by the dichroic mirror.

By using the wavelength demultiplexing optical system, the wavelength converting optical system, and the wavelength multiplexing optical system of the waveguide type as in the second embodiment, the effects similar to those of the first embodiment are obtained. In addition, alignment adjustment becomes unnecessary.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A medical laser apparatus for irradiating an affected tissue with a laser beam to treat the affected tissue, comprising:
   a laser source unit comprising an excitation light source and a Raman fiber, the laser source unit being configured to cause light from the excitation light source to enter the Raman fiber to produce a fundamental wave infrared beam having a predetermined wavelength width and emit this fundamental wave infrared beam;
   a wavelength demultiplexing optical system which spatially wavelength-disperses the fundamental wave infrared beam emitted from the laser source unit into a plurality of infrared beams within the predetermined wavelength width;

a wavelength converting optical system, including a wavelength converting element including a single nonlinear crystal and for wavelength-converting each of the infrared beams demultiplexed by the wavelength demultiplexing optical system to second harmonic wave visible single color beams each of the infrared beams being caused to enter different portions of the nonlinear crystal and then be wavelength-converted to the visible single color beams;

a wavelength multiplexing optical system which multiplexes each of the visible single color beams obtained by the wavelength conversion by the wavelength converting optical system;

a beam stopper which absorbs the infrared beams not wavelength-converted by the wavelength converting optical system; and a delivery optical system which guides each of the visible single color beams multiplexed by the wavelength multiplexing optical system to the affected tissue.

2. The medical laser apparatus according to claim 1, wherein the nonlinear crystal has polarization inverting period structures satisfying quasi phase matching formed continuously or step by step in correspondence with the wavelength of each infrared beam demultiplexed by the wavelength demultiplexing optical system.

3. The medical laser apparatus according to claim 1, wherein the nonlinear crystal has polarization inversion period structure formed based on fluctuation amounts of the wavelength of each infrared beam demultiplexed by the wavelength demultiplexing optical system.

4. The medical laser apparatus according to claim 1, wherein the wavelength demultiplexing optical system and the wavelength multiplexing optical system include a prism respectively.

5. The medical laser apparatus according to claim 1, wherein the wavelength demultiplexing optical system and the wavelength multiplexing optical system include an arrayed waveguide grating respectively.

6. The medical laser apparatus according to claim 5, wherein the nonlinear crystal is formed with waveguides corresponding to waveguides of the arrayed waveguide grating.

7. The medical laser apparatus according to claim 1, wherein the nonlinear crystal includes MgO:PPLN crystal.

* * * * *